(12) United States Patent
Azar (10) Patent No.: US 11,865,336 B2
(45) Date of Patent: Jan. 9, 2024

(54) APPARATUS AND METHOD FOR COSMETIC TREATMENT OF HUMAN MUCOSAL TISSUE (71) Applicant: POLLOGEN LTD., Tel Aviv (IL)

(72) Inventor: Zion Azar, Shoham (IL)

(73) Assignee: POLLOGEN LTD., Tel Aviv (IL)

(*) Notice: Subject to any disclaimer, the term of this patent is extended or adjusted under 35 U.S.C. 154(b) by 0 days.

(21) Appl. No.: 17/889,621

(22) Filed: Aug. 17, 2022

(65) Prior Publication Data

US 2023/0037878 A1 Feb. 9, 2023

Related U.S. Application Data (63) Continuation of application No. 14/970,585, filed on Dec. 16, 2015, now Pat. No. 11,590,346, which is a
(Continued)

(51) Int. Cl.
*A61N 1/36* (2006.01)
*A61N 1/05* (2006.01)
(Continued)

(52) U.S. Cl.
CPC ...... *A61N 1/36007* (2013.01); *A61B 18/1485* (2013.01); *A61N 1/0512* (2013.01);
(Continued)

(58) Field of Classification Search
CPC .............. A61N 1/36007; A61N 1/0512; A61N 1/0524; A61N 1/40; A61N 5/0603;
(Continued)

(56) References Cited

U.S. PATENT DOCUMENTS 2,444,173 A 6/1948 St. Pierre
3,297,024 A 1/1967 Robinson
(Continued)

FOREIGN PATENT DOCUMENTS

CN 1721010 1/2006
EP 1568395 8/2005
(Continued)

OTHER PUBLICATIONS

Godfrey, Sheila, "10 Electricity" In: "Principles and Practice of Electricall Epilation", Oct. 16, 2001, Butterworth Heinemann, pp. 75-83.
(Continued)

*Primary Examiner* — Quang D Thanh
(74) *Attorney, Agent, or Firm* — ISUS INTELLECTUAL PROPERTY PLLC; Anthony Jason Mirabito (57) ABSTRACT

A device for providing fractional treatment of a body orifice includes a source of fractionated energy and a source of electrical muscle (EMS) energy. A programmed controller controls the application of fractionated and/or EMS energy. A probe is inserted by its distal end into the body orifice. The source of fractionated energy is positioned for transmitting fractionated energy from the source of fractionated energy through the probe to tissue in the vicinity around the body orifice; and, the source of EMS is positioned for transmitting EMS energy from the source of EMS energy through the probe to tissue in the vicinity around the body orifice. The programmed controller is configured to control the activation of fractionated energy and EMS energy one of simultaneously or sequentially.

11 Claims, 4 Drawing Sheets

Related U.S. Application Data continuation-in-part of application No. 13/510,062, filed as application No. PCT/IL2010/000947 on Nov. 16, 2010, now abandoned.

(60) Provisional application No. 61/261,381, filed on Nov. 16, 2009.

(51) Int. Cl.
    *A61N 1/40*     (2006.01)
    *A61N 5/06*     (2006.01)
    *A61B 18/14*     (2006.01)
    *A61N 7/00*     (2006.01)
    *A61B 18/00*     (2006.01)

(52) U.S. Cl.
    CPC ............. *A61N 1/0524* (2013.01); *A61N 1/40* (2013.01); *A61N 5/0603* (2013.01); *A61B 2018/005* (2013.01); *A61B 2018/00559* (2013.01); *A61B 2018/00994* (2013.01); *A61B 2018/1435* (2013.01); *A61N 2005/0608* (2013.01); *A61N 2005/0611* (2013.01); *A61N 2007/0043* (2013.01)

(58) Field of Classification Search
    CPC .... A61N 2005/0608; A61N 2005/0611; A61N 2007/0043; A61B 18/1485; A61B 2018/005; A61B 2018/00559; A61B 2018/00994; A61B 2018/1435
    See application file for complete search history.

(56) References Cited

U.S. PATENT DOCUMENTS

| | | | |
|---|---|---|---|
| 4,702,732 A | 10/1987 | Powers et al. | |
| 5,169,398 A | 12/1992 | Glaros | |
| 5,296,683 A | 3/1994 | Burkett et al. | |
| 5,419,344 A | 5/1995 | DeWitt | |
| 5,476,504 A | 12/1995 | Paolizzi | |
| 5,562,706 A | 10/1996 | Lauterbach | |
| 5,755,753 A | 5/1998 | Knowlton | |
| 5,797,904 A | 8/1998 | Smith | |
| 5,797,966 A | 8/1998 | Bontoux | |
| 5,961,475 A | 10/1999 | Guity | |
| 6,139,545 A | 10/2000 | Utely | |
| 6,185,465 B1 * | 2/2001 | Mo | A61B 5/391 264/250 |
| 6,273,884 B1 | 8/2001 | Altshuler et al. | |
| 6,277,116 B1 | 8/2001 | Utely | |
| 6,296,683 B1 | 10/2001 | Koch | |
| 6,425,912 B1 | 7/2002 | Knowlton | |
| 6,546,934 B1 | 4/2003 | Ingle et al. | |
| 6,692,490 B1 | 2/2004 | Edwards | |
| 6,840,954 B2 | 1/2005 | Dietz et al. | |
| 7,953,500 B2 | 5/2011 | Bingham et al. | |
| 9,596,920 B2 | 3/2017 | Shalev et al. | |
| 2001/0014815 A1 | 8/2001 | Matsumura et al. | |
| 2002/0032441 A1 | 3/2002 | Ingle | |
| 2002/0120260 A1 | 8/2002 | Morris et al. | |
| 2003/0032950 A1 | 2/2003 | Altshuler | |
| 2003/0083590 A1 * | 5/2003 | Hochman | A61B 5/14539 600/549 |
| 2003/0187488 A1 | 10/2003 | Kreindel | |
| 2004/0019350 A1 | 1/2004 | O'Brien | |
| 2004/0073079 A1 | 4/2004 | Altshuler | |
| 2004/0220622 A1 | 11/2004 | Bernabei | |
| 2005/0015085 A1 | 1/2005 | McClurken et al. | |
| 2005/0107832 A1 | 5/2005 | Bernabei | |
| 2005/0154433 A1 | 7/2005 | Levy, Jr. | A61B 18/1485 607/101 |
| 2005/0171583 A1 | 8/2005 | Mosher | A61B 17/0625 607/96 |
| 2005/0222565 A1 | 10/2005 | Manstein | |
| 2006/0036300 A1 | 2/2006 | Kreindel | |
| 2006/0205996 A1 | 9/2006 | Presthus | A61B 5/1076 600/29 |
| 2006/0206103 A1 | 9/2006 | Altshuler | |
| 2006/0206110 A1 | 9/2006 | Knowlton et al. | |
| 2006/0217704 A1 | 9/2006 | Cockburn et al. | |
| 2007/0055154 A1 | 3/2007 | Torbati | |
| 2007/0055180 A1 | 3/2007 | Deem | |
| 2007/0060989 A1 | 3/2007 | Deem | A61B 18/1477 607/99 |
| 2007/0179490 A1 | 8/2007 | Azar | |
| 2007/0198004 A1 | 8/2007 | Altshuler | |
| 2007/0232966 A1 | 10/2007 | Applebaum et al. | |
| 2008/0039914 A1 | 2/2008 | Cory | |
| 2008/0103565 A1 | 5/2008 | Altshuler et al. | |
| 2008/0215039 A1 | 9/2008 | Slatkine | |
| 2008/0312646 A9 | 12/2008 | Peterson | |
| 2008/0312648 A1 | 12/2008 | Peterson | |
| 2009/0043293 A1 | 2/2009 | Pankratov | A61B 18/203 606/9 |
| 2009/0156958 A1 | 6/2009 | Mehta et al. | |
| 2009/0270963 A1 | 10/2009 | Pelger | A61B 5/04882 607/138 |
| 2010/0016850 A1 | 1/2010 | Ron Edoute | |
| 2010/0049186 A1 | 2/2010 | Ingle et al. | |
| 2010/0057149 A1 | 3/2010 | Fahey | |
| 2010/0174137 A1 | 7/2010 | Shim | A61F 5/41 600/38 |
| 2010/0228304 A1 | 9/2010 | Kriksunov et al. | |
| 2011/0009692 A1 | 1/2011 | Gross | A61N 1/0524 600/38 |
| 2011/0130618 A1 | 6/2011 | Ron Edoute | |
| 2011/0224665 A1 | 9/2011 | Crosby et al. | |
| 2011/0230931 A1 | 9/2011 | Hagege | A61B 5/063 607/41 |
| 2012/0215141 A1 | 8/2012 | Peddicord | A61H 19/00 601/46 |
| 2012/0027120 A1 | 10/2012 | Shalev et al. | |
| 2012/0271206 A1 | 10/2012 | Shalev et al. | |
| 2013/0018222 A1 | 1/2013 | Miroshnichenko | A61H 19/32 600/38 |
| 2013/0274823 A1 * | 10/2013 | Hagege | A61N 1/36007 607/41 |
| 2015/0164401 A1 | 6/2015 | Toth | A61B 5/04882 600/301 |
| 2015/0297908 A1 | 10/2015 | Alinsod | A61N 1/403 607/102 |
| 2016/0121112 A1 | 5/2016 | Zion | |
| 2016/0263387 A1 | 9/2016 | Alinsod | A61N 1/403 |
| 2016/0346561 A1 | 12/2016 | Ron Edoute | |
| 2016/0346568 A1 | 12/2016 | Rockweiler | A61B 5/01 |
| 2017/0014395 A1 | 5/2017 | Shalev et al. | |
| 2017/0143997 A1 | 5/2017 | Rockweiler | A61B 5/01 |
| 2017/0023946 A1 | 8/2017 | Shalev et al. | |
| 2021/0002336 A1 | 1/2021 | Shalev et al. | |
| 2022/0018438 A1 | 6/2022 | Shalev et al. | |
| 2022/0022664 A1 | 7/2022 | Shalev et al. | |
| 2022/0226646 A1 | 7/2022 | Shalev et al. | |
| 2022/0226647 A1 | 7/2022 | Shalev et al. | |
| 2022/0226648 A1 | 7/2022 | Shalev et al. | |
| 2022/0226649 A1 | 7/2022 | Shalev et al. | |
| 2022/0233851 A1 | 7/2022 | Shalev et al. | |
| 2022/0028078 A1 | 9/2022 | Shalev et al. | |

FOREIGN PATENT DOCUMENTS

| | | |
|---|---|---|
| EP | 2476460 | 7/2012 |
| GB | 277882 | 9/1927 |
| JP | H119703 | 1/1999 |
| JP | 3041670 | 5/2000 |
| JP | 2001259047 | 9/2001 |
| JP | 2003010145 | 1/2003 |
| JP | 2003019215 | 1/2003 |
| JP | 2004522497 | 7/2004 |
| JP | 2007507317 | 3/2007 |
| JP | 2006520247 | 9/2007 |
| JP | 2008173231 | 7/2008 |
| JP | 2008537896 | 10/2008 |

(56) References Cited

FOREIGN PATENT DOCUMENTS

| | | |
|---|---|---|
| JP | 2008545462 | 12/2008 |
| JP | 2012065693 | 4/2012 |
| RU | 2153366 | 7/2000 |
| RU | 2005131621 | 2/2006 |
| WO | 0112089 | 2/2001 |
| WO | 2008058452 | 5/2008 |
| WO | 2009023568 | 2/2009 |
| WO | 2012080394 | 6/2012 |
| WO | 2015014811 | 2/2015 |

OTHER PUBLICATIONS

Y.Y. Dribnokhod, Cosmetology, Rostov-on-Don, "Fenix", 2008, pp. 384-385.
Extended European Search Report—Corresponding European Application No. 16875059.4, dated Nov. 29, 2018, 9 pages.
Supplementary European Search Report for Application No. EP10829624.5, dated Jan. 29, 2015.
European Office Action for Application No. EP10829624.5, dated Feb. 20, 2015.
Russian Office Action from Application No. 2012123457, dated Sep. 19, 2014.
Japanese Office Action from Application No. 2012-538469, dated Sep. 16, 2014.
Chinese Office Action from Application No. 201080051957.9, dated Jun. 4, 2014.
Office Action for Australian Patent Application No. 2010317380 dated May 14, 2014.
International Search Report for Application No. PCT/IL2010/000947, dated Apr. 5, 2011.

* cited by examiner

APPARATUS AND METHOD FOR COSMETIC TREATMENT OF HUMAN MUCOSAL TISSUE

RELATED APPLICATIONS

The present application is related to, claims priority to and is a continuation application of U.S. application Ser. No. 14/970,585, filed Dec. 16, 2015, which is a continuation in part of U.S. application Ser. No. 13/510,062, filed May 16, 2012, which is a 371 national phase application of PCT/IL10/00947, filed Nov. 16, 2010, which claims priority to U.S. Provisional Application Ser. No. 61/261,381, filed Nov. 16, 2009, the entirety of which are hereby incorporated by reference.

FIELD OF THE INVENTION

The present invention relates to the use of one or more treatment modalities in the cosmetic treatment of human mucosal tissue to provide, among other things, vaginal and anal tightening and urinary incontinence treatment.

BACKGROUND OF THE INVENTION

Vaginal Relaxation Syndrome (VRS) commonly called "loose vagina" is a quite common medical condition described as a loss of the optimal vaginal structure and is usually associated with vaginal child delivery and natural aging.

Multiple pregnancies and deliveries contribute to a worsening of the VSR condition, as well as the beginning of menopause, which causes a decline in hormone levels and vaginal atrophy.

Most women and their husbands or partners refer to VSR as "loose vagina", complaining of a loss of vaginal tightness, which is directly related to the reduction of friction during intercourse and thus to a decrease or loss of sexual gratification.

There is a large spectrum of various VRS treatment options on the market ranging from behavioral (Kegel exercises) through pharmacological therapies (hormonal, tightening creams and sprays) to various more-or-less invasive surgical procedures.

While behavioral and pharmacological therapies are non-invasive and safe, they have limited efficacy.

On the other hand, various surgical procedures promise a much better final result at the price of higher associated risks.

Surgical procedures require the cutting and rearrangement of vaginal and peripheral tissue in order to reduce the size of the vaginal canal.

Operating on or near sensitive vaginal tissue is inherently risky and can cause scarring, nerve damage and decreased sensation. Furthermore, patients require an extended recovery period.

The most popular among the surgical procedures are those performed with lasers, where the laser is used instead of scalpel.

Thus there is a clear need for efficient noninvasive solutions for vaginal rejuvenation.

Numerous techniques have been described for tissue rejuvenation mostly for skin treatment. For example, U.S. Pat. No. 6,387,089 describes a procedure referred to as photo rejuvenation, wherein pulsed light is used for heating and shrinking the collagen and thereby restoring the elasticity of the skin. Since collagen is located in the dermis, lasers that target collagen must penetrate through the epidermis and through the dermal epidermal junction. Due to Bier's Law of absorption, the laser beam is typically most intense at the surface of the skin. This results in unacceptable heating of the upper layers of the skin. Various approaches have been described to cool the upper layers of the skin while maintaining the layers underneath at the desired temperature. One approach is to spray a cryogen material on the surface so that the surface remains cool while the underlying layers (and hence collagen) are heated. Such an approach is described in U.S. Pat. No. 6,514,244. Another approach, described in U.S. Pat. No. 6,387,089, is the use of a cooled transparent substance, such as ice, gel or a crystal that is in contact with the surface of the skin. The transparent nature of the coolant allows the laser beam to penetrate the different skin layers while maintaining an acceptable temperature level on the surface of the skin.

An objective of non-ablative photo-rejuvenation is to induce a thermal wound repair response in the papillary and upper reticular dermal compartments (approximately 100-400 micro-meter below the surface of the skin) while sparing the epidermal compartment.

To overcome some of the problems associated with the undesired heating of the upper layers of the skin (epidermal and dermal) described above, U.S. Pat. No. 6,311,090 describes using RF energy and an arrangement comprising RF electrodes that rest on the surface of the skin. A reverse thermal gradient is created that apparently does not substantially affect melanocytes and other epithelial cells. However, even such noninvasive methods have the significant limitation in that energy cannot be effectively focused in a specific region of interest for example the dermis.

Other approaches have been described to heat the dermis without heating more superficial layers. These involve using electrically conductive needles that penetrate the surface of the skin into the tissue and provide heating. U.S. Pat. Nos. 6,277,116 and 6,920,883 describe such systems. Unfortunately, such an approach results in widespread heating of the subcutaneous layer and potentially melting the fat in the subcutaneous layer. This leads to undesired scarring of the tissue.

One approach that has been described to limit the general, uniform heating of the tissue is fractional treatment of the tissue, as described in U.S. Patent Application publication No. 2005/0049582. This application describes the use of laser energy to create treatment zones of desired shapes in the skin, where untreated, healthy tissue lies between the regions of treated tissue. This enables the untreated tissue to undergo a healing and recovery process.

As opposed to traditional laser resurfacing, which treats the whole surface of the target tissue, fractional laser skin resurfacing uses fractional Photothermolysis. It targets tissue with a pattern of dispersed spots. This results in a pattern of microscopic zones of tissue coagulation that heal over several weeks while the skin retains normal appearance. Rather than creating a global tissue effect at the surface of the target tissue, or in the dermis alone, this method creates injury in a small fraction of the skin treated, coagulating multiple columns of tissue, generally 70-100 micron in diameter, extending through the epidermis and deep into the dermis reaching up to generally 1 mm depth. These laser columns create micro thermal zones of tissue coagulation which is surrounded by healthy tissue. The healthy tissue provides a generous reservoir of stem cells and melanocytes in the papillary dermis that are spared from wounding and accelerate the healing process. The small size of the wounds and the short migratory paths for keratinocytes from the spared tissue result in rapid re-epitheliazation and fast epidermal repair. Zones of collagen denaturation in the dermis cause upregulation of the inflammatory cascade, which leads to collagen remodeling to depths of generally 400-700 microns resulting in skin tightening. The fact that patients do not have open wounds leads to minimal downtime. Fractional laser resurfacing is therefore a non-ablative procedure. It offers improved skin texture, tone, pigmentation, fine lines and skin tightening. Fractional resurfacing requires a series of 3-5 treatments as opposed to ablative lasers that require a single treatment.

Fractional vaginal rejuvenation systems exist in the market using CO2 or Er:YAG lasers. These include, for example, IntimaLase by Fotona—a minimally-invasive, non-ablative Er:YAG laser vaginal tightening procedure utilizing photothermal laser-mucosa tissue interaction. Another device is FemiLift by Alma Laser. This is a non-invasive Laser Vaginal Tightening device using CO2 laser by thermal heating of the vaginal tissue inner layers inducing collagen and elastin contraction and regeneration of the proteins over time.

Disadvantages of such known fractional laser resurfacing systems include: they are cumbersome and expensive. As well, in order to achieve dramatic results heating of the tissue reaches the temperature in the necrotic zone which is around 70° C., and the tissue, whether it is made up primarily of cells, keratinocytes and their derivatives or collagen, is necrosed or denatured, respectively. Temperatures in the tissue above 100° C. may cause steam to form in the tissue, which may cause disruptive effects. Such temperatures may result in undesirable side effects such as pain, erythema, swelling, occasional scarring, extended healing times and infection.

Thus there is an unmet need for a simple, inexpensive fractional treatment of the vagina that causes tissue injury and triggers tissue healing processes but without the risks and complications caused by tissue heating that creates denaturation and coagulation of tissue. While the present invention may be administered within the confines of a physician's or other operator's office environment, it is of sufficiently simple operation that it may be used in the privacy of the user's home. For example, the present invention may have a switch or other device so that the EMS function may be separable from the RF function so that a user can activate the EMS portion of the present apparatus without activating the RF function for training and/or vaginal tightening purposes.

SUMMARY OF THE INVENTION

In an aspect, a device which provides fractional treatment of a body orifice includes a source of fractionated energy; a source of electrical muscle (EMS) energy; a programmed controller to control the application of fractionated and/or EMS energy; a probe for insertion of its distal end into the body orifice. The source of fractionated energy is positioned for transmitting fractionated energy from the source of fractionated energy through the probe to tissue in the vicinity around the body orifice; and, the source of EMS is positioned for transmitting EMS energy from the source of EMS energy through the probe to tissue in the vicinity around the body orifice; the programmed controller is configured to control the activation of fractionated energy and EMS energy one of simultaneously or sequentially.

In another aspect, the body orifice may be selected from one of: a vaginal cavity; an anal cavity, the oral cavity or the aural cavity, and the treatment provides one of vaginal or anal tightening.

In a further aspect, the fractionated energy is radio frequency (RF) energy or Ultrasound (US) energy or it may be light energy.

In yet another aspect, the controller may be configured to activate the EMS energy first, followed by activation of the RF energy, whereby the tissue in the vicinity of the body orifice is first drawn into contact with the probe, followed by activation of RF energy. The controller may activate the application of EMS energy and then RF energy a selected number of times.

In a further aspect, the source of fractionated energy may include electrodes mounted on an outer surface of the probe and may be mounted in the form of one or more spirals along the other surface of the probe. The device may be for home use.

In yet another aspect, a method is providing for the fractional treatment of a body orifice and includes: transmitting fractionated energy from a source of fractionated energy through a probe inserted in the body orifice to tissue in the vicinity around the body orifice; and, transmitting EMS energy from a source of EMS energy through the probe to tissue in the vicinity around the body orifice.

In yet a further aspect, a programmed controller is configured to control the transmitting of the one or more of fractionated and EMS energy one of simultaneously or sequentially. The controller may activate the EMS energy first, followed by activation of the RF energy, whereby the tissue in the vicinity of the body orifice is first drawn into contact with the probe, followed by activation of RF energy. The controller may activate the application of EMS energy and then RF energy a selected number of times. The method may be practiced in one of an office or a home use.

In another aspect, the programmed controller may be configured to control the activation of fractionated energy and/or the EMS energy. The EMS energy may be activated and the fractionated energy source not activated for purposes of tightening the body orifice, including vaginal or anal tightening.

DETAILED DESCRIPTION OF THE PRESENT INVENTION

One aspect of the present invention is providing a system and method of treatment for vaginal tightening. The system, shown in FIG. 1 as reference numeral 10, includes a vaginal probe 12 which can be inserted into the vagina and is configured to provide a combination of two types of electrical signals to the vagina wall (not shown). The system 10 also includes a power supply unit 14, a programmable controller 16 with a graphic user interface (GUI) 18. Connected to the controller are an electrical muscle stimulation (EMS) unit 20 and a radio frequency (RF) unit 22, both of which may be selectively actuated to provide their respective energy inputs to the probe 12 under the control of the controller 16. In addition, pressure sensor 24 and temperature sensor 26 may be provided to provide feedback from the probe 12 before and/or during and/or after either one or both of the EMS unit and/or the RF unit are activated under control of the controller 16. The feedback may include, by way of example only, as a measurement of the efficiency of the treatment in terms of time and extent of treatment. A first electrical signal applied is, as mentioned above, an electrical muscle stimulation signal (EMS) which is purposed and designed when activated to contract the vaginal smooth muscle around a vaginal probe 12. A second electrical signal is, again as mentioned above, a radio frequency (RF) signal which is purposed and designed when activated under control of the controller to irradiate the vaginal tissue. U.S. application Ser. No. 13/510,062, which is incorporated herein by reference to this application, further describes possible combinations for providing the signals to a target tissue.

Figure 3:
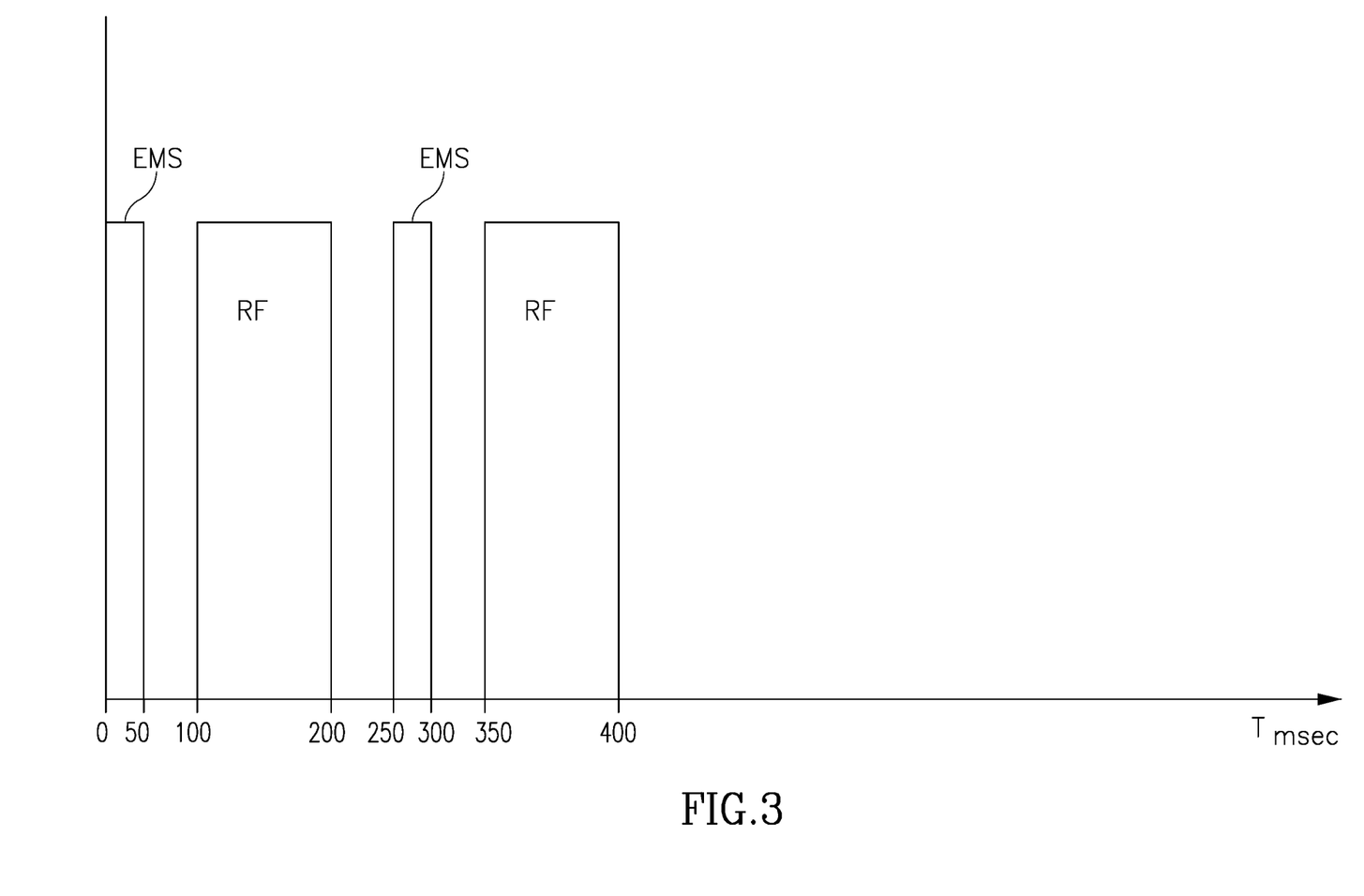
FIG. 3 graphically illustrates the operation of the system of the present invention in the provision of RF and EMS energy.

Referring now to FIG. 3, a sequence of EMS pulses followed by a RF pulse is shown. The EMS pulse serves to contract the vagina around the vaginal probe to create a proper electrical coupling between the inner vaginal tissue and the electrodes. In addition, the pressure sensor 24 may be incorporated on the vaginal probe to measure to feedback for the pressure created by the vagina on the probe 12. The amount of pressure sensed may provide an indication of adequate or inadequate coupling of electrodes. The EMS pulses applied activate the muscle and flatten the mucosal tissue such that the muscle are closer to the surface of the electrodes. The controller may be disabled from activating the RF unit 22 until a selected pressure reading is detected, for example. Alternatively, tissue impedance measurement by the treating electrodes by a set of dedicated electrodes may also be used, as known to those skilled in the art, to provide a feedback for the tissue-electrode coupling. Furthermore, the temperature sensor 26 may provide temperature readings at the probe/vagina wall interface to make sure excessive heating does not occur. Excessive heating of the vagina tissue may cause the controller to stop activation of the EMS and/or RF units.

Back to the pulse sequence in FIG. 3, a treatment RF pulse is initiated after the EMS signal. The EMS signals may be relatively short and may be in the range of 50-350 microsec. This signal may be repeated in a frequency of about 5-25 Hz. The temperature sensor 26 may feedback to the controller 16 which is configured to control the RF pulse width.

RF may be bipolar or monopolar. In a monopolar configuration, an external electrode on the pubis or lower back may be used. EMS signals may use a dedicated electrode or the same electrodes used for the RF unit. In such a case, a diode bridge known to those skilled in the art may be provided to "cut" the AC RF signals to produce an effective DC signal in the range of 1 to 30 milliseconds. This configuration makes the whole system much simpler and easier to implement as a home-use device. The DC EMS signal may cause the muscle to be smoothed out which in turn may induce contraction.

According to one aspect of the invention, the system is configured to switch between EMS and RF signals. An EMS signal followed by a RF treatment signal may create thermal damage to the adjacent vaginal tissue and cause its tightening. According to another embodiment of the present invention, RF only or EMS only signal may be used in order to heat or exercise the vagina respectively. According to yet another embodiment of the present invention, the order of the application of RF and EMS pulses may be in any order or sequence desired to achieve desirable treatment results.

Figure 2A:
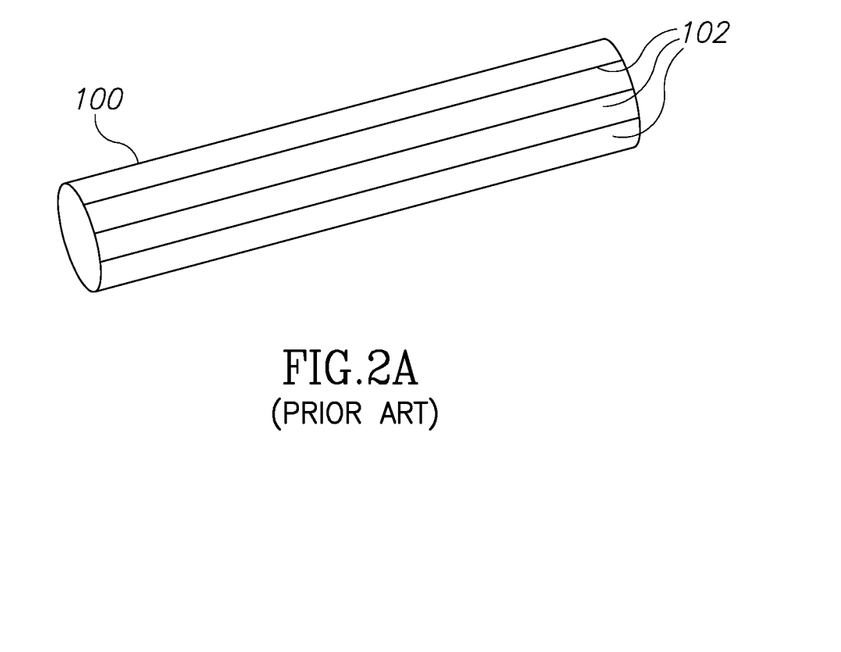
FIGS. 2A and 2B illustrate a prior art probe and a probe of the present invention which may be utilized in connection with the system of the present invention.
Figure 2B:
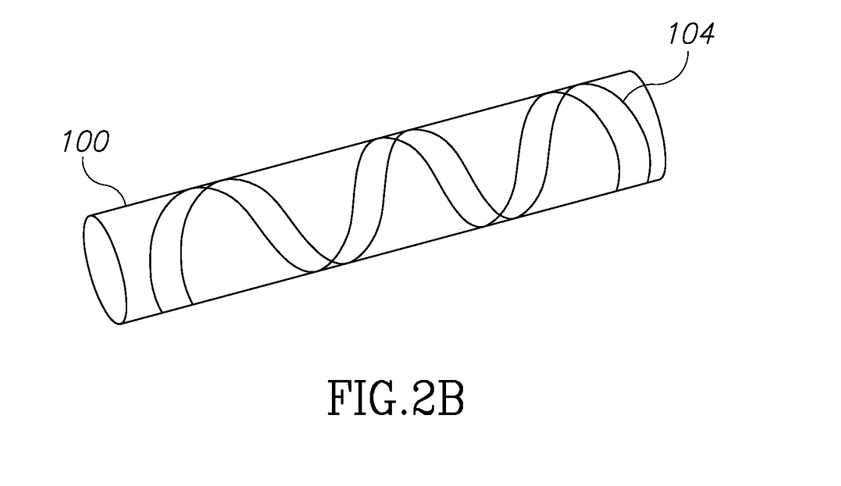

The vagina is a hollow organ and is comprised of a smooth muscle. Smooth muscles are characterized by high elasticity which gives them the ability to stretch while still maintaining strong contractability. Smooth muscle cell cytoplasm is rich with myosin and actin molecules which provide a smooth muscle cell the ability to contract. Tensile structure between smooth muscle cells contains actin filaments of contractile units which are attached to dense bodies creating a network of contracting fibers. This network is neither in a parallel line orientation across nor along the vagina smooth muscle, rather in a more diagonal orientation. As a result, smooth muscle tends to contract in a spirally. Therefore, the most effective way to induce a stimulation of a smooth muscle may not be by providing parallel electrodes 102 along or across a prior art vaginal probe 100 shown in FIG. 2A which is known in the VDR technology by Nova-Clinical from Italy. As shown in FIG. 2B, one or more spiral electrodes 104 are mounted or otherwise fixed onto and along a vaginal probe 1016. Spirally-oriented electrodes are believed to better suited to create an effective stimuli vector in a contacting spot, given the anatomy and arrangement of the contracting fibers in the smooth muscle of the vagina.

Figure 1:
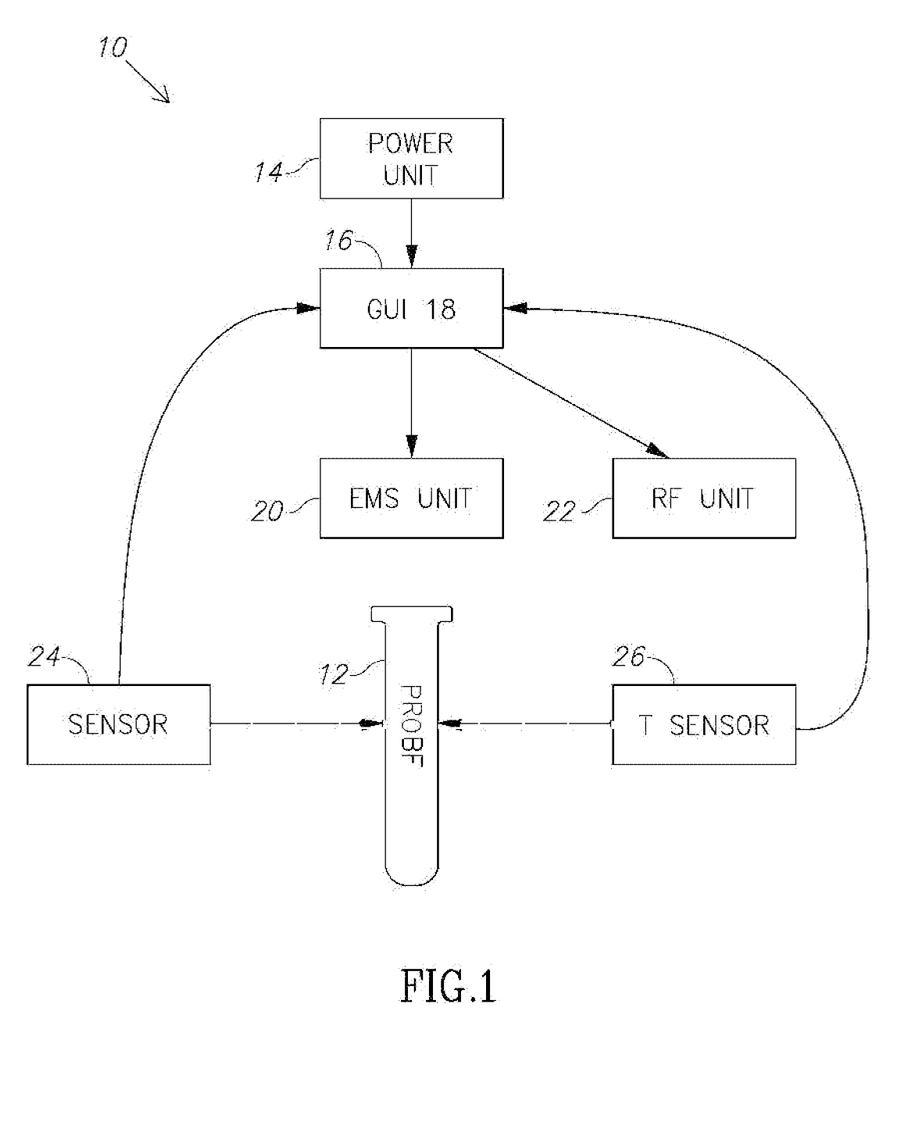
FIG. 1 illustrates an overall schematic diagram of the system of the present invention.
Figure 2C:
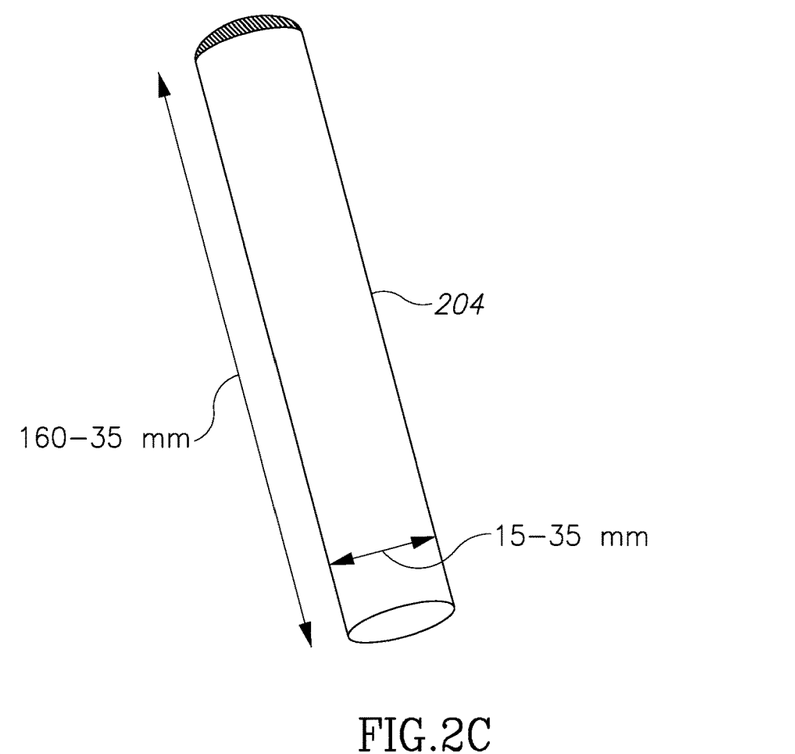
FIGS. 2C through 2D illustrate a holder/mounter system for holding/mounting the probe of the present invention in situ.
Figure 2D:
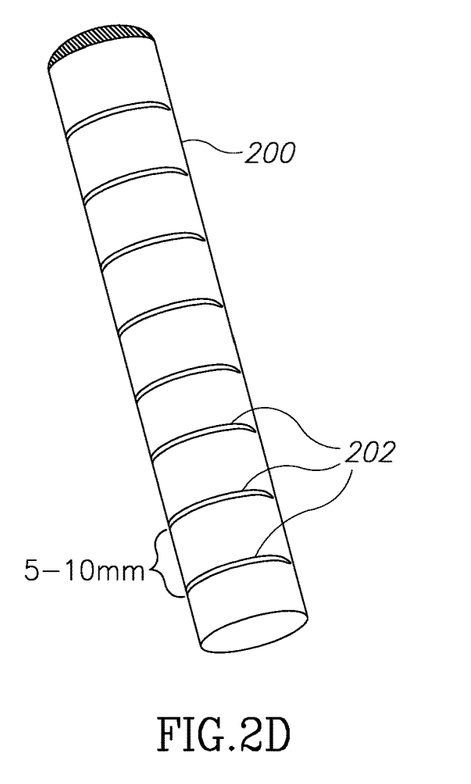

Turning now to FIGS. 2C and 2D, these figures illustrate arrangements of jackets in which the vagina probe 12 of FIG. 1 may be inserted. FIG. 2D illustrates a probe 200 with measurement markings 202, which may be every 5-10 mm. The probe 200 may fit inside a sleeve 204 as shown in FIG. 2C. The design of the combined unit includes insertion of the sleeve 204 into the vagina. The probe 200 may then be inserted into the sleeve and thus vagina of the patient. A portion of the sleeve 204 will remain outside of the patient's body and the doctor or other operator can read the degree of insertion by reading the measurement markings at position 202. This arrangement allows the doctor or other operator to selectively and/or sequentially treat various depths into the patient's vagina.

As mentioned above, it is known to provide light-based vaginal rejuvenation treatments. However, what is not believed to be known is the combination of EM treatment combined with EMS treatment, so that the tissue surrounding the inserted probe will be drawn into contact with the probe in order to provide more effective and efficient treatment of the vaginal walls due to the close contact with the probe and thus the source of energy.

The invention claimed is:

1. A device for providing tissue tightening treatment of a body orifice, the device comprising:
   a source of radio frequency (RF) energy;
   a source of electrical muscle stimulation (EMS) energy;
   a probe having a distal end configured for insertion into the body orifice, the probe comprising at the distal end an external surface carrying:
      at least one electrode being in communication with the source of RF energy and the source of EMS energy and configured for feeding the RF and EMS energies to internal wall of the body orifice;
      a temperature sensor configured to read temperature of the internal wall before, during and after the treatment; and
      a pressure sensor configured to measure pressure created by the internal wall on the external surface before and during the treatment;

and a programmed controller configured to receive feedback from the temperature and pressure sensors and control application of the RF and EMS energies.

2. The device of claim 1, wherein said controller is configured to activate the EMS energy source first and then activate the RF energy source based on the feedback from the pressure sensor indicating adequate coupling of the at least one electrode with the internal wall.

3. The device of claim 1, wherein said controller is configured to control activation and deactivation of the RF energy source, RF pulse width and extent of treatment based on the feedback received from the temperature sensor.

4. The device of claim 1, wherein said controller is configured to activate the RF and EMS sources simultaneously for at least some of time of the treatment.

5. The device of claim 1, wherein the controller is configured to activate the EMS energy and the RF energy sources sequentially for a selected number of times and for selected respective durations, based on the feedback from the pressure and temperature sensors.

6. The device of claim 1, wherein said at least one electrode is configured for applying both of the RF and EMS energies, the device further comprising a diode bridge configured for selectively blocking alternating current (AC) signals and providing an effective direct current (DC) signal through the at least one electrode when the EMS energy is applied.

7. The device of claim 1, wherein said at least one electrode comprises at least two electrodes, said RF energy is applied in a bipolar configuration utilizing said at least two electrodes.

8. The device of claim 1, wherein said RF energy is applied in a monopolar configuration, wherein said device comprises an external electrode configured for placing on external surface of the body.

9. The device of claim 1, wherein said at least one electrode comprises a plurality of electrodes distributed over the external surface in one or more spirals.

10. The device of claim 1, further comprising a sleeve configured for insertion into the body orifice, wherein the probe is configured for insertion into the sleeve, the sleeve thereby enabling controlling depth of insertion of the device into the body orifice.

11. The device of claim 1, wherein the body orifice is selected from one of: a vaginal cavity; an anal cavity, an oral cavity or an aural cavity.

* * * * *